United States Patent [19]

Dahlgren et al.

[11] Patent Number: 4,553,985
[45] Date of Patent: Nov. 19, 1985

[54] GAS CHROMATOGRAPHY

[75] Inventors: Robert W. Dahlgren; William H. Dennis, both of Bartlesville, Okla.

[73] Assignee: Phillips Petroleum Company, Bartlesville, Okla.

[21] Appl. No.: 583,469

[22] Filed: Feb. 24, 1984

[51] Int. Cl.⁴ .............. B01D 15/08; G01N 31/08
[52] U.S. Cl. .......................... 55/67; 55/197; 55/386; 73/23.1
[58] Field of Search .............. 55/67, 197, 386; 73/23.1

[56] References Cited

U.S. PATENT DOCUMENTS

| | | | |
|---|---|---|---|
| 2,841,005 | 7/1958 | Coggeshall | 73/23.1 |
| 2,893,955 | 7/1959 | Coggeshall | 55/67 X |
| 3,030,798 | 4/1962 | Lichtenfels | 73/23.1 |
| 3,069,897 | 12/1962 | Sanford | 55/67 X |
| 3,087,112 | 4/1963 | Pfefferle | 73/23.1 X |
| 3,097,519 | 7/1963 | Favre | 73/23 |
| 3,152,470 | 10/1964 | Reinecke et al. | 73/23.1 |
| 3,264,801 | 8/1966 | Buhl et al. | 55/67 |
| 3,330,150 | 11/1967 | Loyd et al. | 73/23.1 |
| 3,394,582 | 7/1968 | Munro et al. | 73/23.1 |
| 3,449,938 | 6/1969 | Giddings | 55/67 X |
| 3,470,676 | 10/1969 | Kabot | 55/67 |
| 3,514,262 | 5/1970 | Ayers et al. | 23/230 |
| 3,550,429 | 12/1970 | MacMurtrie et al. | 73/23.1 |
| 4,007,626 | 2/1977 | Roof et al. | 73/23.1 |
| 4,215,563 | 8/1980 | Clardy et al. | 73/23.1 |
| 4,271,697 | 6/1981 | Mowery, Jr. | 55/67 X |
| 4,287,752 | 9/1981 | Ury | 73/23.1 |
| 4,359,891 | 11/1982 | Ahlstrom, Jr. et al. | 73/23.1 |
| 4,399,688 | 8/1983 | Dennis | 73/23.1 |
| 4,402,832 | 9/1983 | Gerhold | 55/67 X |
| 4,478,721 | 10/1984 | Gerhold | 55/67 X |

OTHER PUBLICATIONS

Barry et al., J. of Chroma. Sci., vol. 20, Aug. 1982, p. 357, "Behavior of Chromatographic Columns . . . ".

Primary Examiner—Robert Spitzer
Attorney, Agent, or Firm—French & Doescher

[57] ABSTRACT

A gas chromatograph in which a first portion of sample peaks are eluted in forward flow mode and a second portion of sample peaks are eluted in reverse flow mode without loss of resolution.

22 Claims, 2 Drawing Figures

GAS CHROMATOGRAPHY

BACKGROUND OF THE INVENTION

This invention relates to chromatographic analysis. In one aspect, the invention relates to chromatographic analysis of gas samples. In another aspect, the invention relates to an apparatus for carrying out a chromatographic analysis of a gas sample.

Many gas streams contain components having discrete individual boiling points which vary over a wide range. Analysis of such streams by gas chromatography, for the purpose of process monitoring, for example, is not always entirely satisfactory due to the excessive time required to elute the higher boiling components from the column. The problem is that the column length and packing required to separate the low boiling component will not allow the elution of the higher boiling components in a time suificiently short for good process control requirements.

Providing a gas chromatographic technique wherein the high boiling components are eluted from the column in a reasonably short period of time would be very desirable.

OBJECTS OF THE INVENTION

It is an object of this invention to provide a gas chromatographic technique for the elution of more components of the gas sample in a shorter period of time than in the usual bypass column arrangement and without the complexity of a programmed temperature manipulation of the gas chromatographic column.

It is another object of this invention to provide a gas chromatography apparatus capable of reduced elution time where the components in the gas stream to be analyzed have a wide range of individual boiling points.

SUMMARY OF THE INVENTION

In one aspect, the invention provides a process for separating the components of the gas sample comprised of a number of components. The sample is introduced into the first end of a chromatographic separation column and eluted toward the second end of the column by a flow of carrier gas. The length and packing of the column are selected such that the components of the sample become distributed along the length of the column. A first fraction of the number of components is eluted from the second end of the column with the carrier gas and this first fraction is conveyed to a detector in the usual manner. At this point, the flow of carrier gas is reversed with respect to the column and the carrier gas is caused to flow from the second end of the column toward the first end. The second fraction of the number of components are eluted from the first end of the column and conveyed to the detector. Because of the nonlinear velocity profile across the column, and this is especially true with a high pressure drop column, component group peaks that were separated along the length of the column in the forward flow mode are not regrouped in the reverse flow mode. This phenomenon is explainable in terms of the gas density variation along the length of the column. The gas is more dense at the high pressure end of the column than at the low pressure end of the column. Yet mass flow at both ends of the column must be the same. In order to have the same mass flow, the low pressure, low density gas must flow faster than the high pressure high density gas. The components thus accelerate as they near the downstream end of the column. Just before the reversal of the carrier gas flow, the peaks nearing the outlet end of the column are traveling much faster than the peaks more retained. Just after the switch in carrier gas flow, the most retained peak is in the highest velocity carrier gas location and will be eluted first. It can be recalled from the column faster than it can traverse it. The phenomenon is used in the invention to elute more components in a shorter time.

In another aspect of the invention, there is provided a gas chromatographic technique. A gaseous sample comprised of light components and heavy components is caused to flow into a sample chamber. A first flow of carrier gas is caused to flow through the sample chamber and into a first end of a chromatographic column having a first end and a second end. The sample is thus conveyed or flushed into the first end of the chromatographic column. In the column, the light components of the sample are eluted from the second end of the column with a first flow of carrier gas. The first flow of carrier gas is then stopped and a second flow of carrier gas initiated from the second end of the column to the first end of the column. The heavy components of the sample are eluted from the first end of the column and the second flow of carrier gas is then terminated.

In a still further aspect of the invention, there is provided an apparatus for carrying out gas chromatography. The apparatus comprises a column which is suitable for use in high pressure gas chromatography and has a first end and a second end. A sample chamber is provided which has a predetermined volume. A detector which can be of the usual type is also present as well as a source of carrier gas. In accordance with the invention, there is provided a first means for establishing a flow path from the source of carrier gas to the sample chamber, through the sample chamber and to the first end of the column. The means is defined on through the column from the first end to the second end and to the detector. A second means for establishing a flow path from the source of carrier gas to the second end of the column, through the column from the second end to the first end, and to the detector is also provided. A means for selectively connecting one of the first means for establishing a flow path and the second means for establishing a flow path and selectively disconnecting the other is also provided so that the apparatus will function for its intended purpose.

In a still further aspect of the invention there is provided a gas chromatography apparatus. The apparatus comprises a sample chamber defined by a first tubular member having an inlet end and an outlet end. The apparatus is further provided with a column suitable for use in high pressure gas chromatography which has a first end and a second end. A first means for defining a flow path connects the sample chamber and the column. A detector which can be of the usual type is also provided. A second means for defining a flow path connects the column and the detector. A first valve means at the inlet end of the first tubular member is switchable from a first position in which the first tubular member can be connected to a source of carrier gas to a second position in which the first tubular member can be connected to a source of sample. A second valve means at the outlet end of the first tubular member is switchable from a first position in which the first tubular member is connected to an exhaust to a second position in which the first tubular member is connected to the means defining a flow path between the sample chamber and the column. The means defining the flow path between the sample chamber and the column includes a third valve means which is switchable from a first position for connecting the first means for defining a flow path to the first end of the column to a second position for connecting the first means for defining a flow path to the second end of the column. The second means for defining a flow path includes a fourth valve means which is switchable from a first position for connecting the second end of the column to the detector to a second position for connecting the first end of the column to the detector.

DETAILED DESCRIPTION OF THE DRAWING

Figure 1:
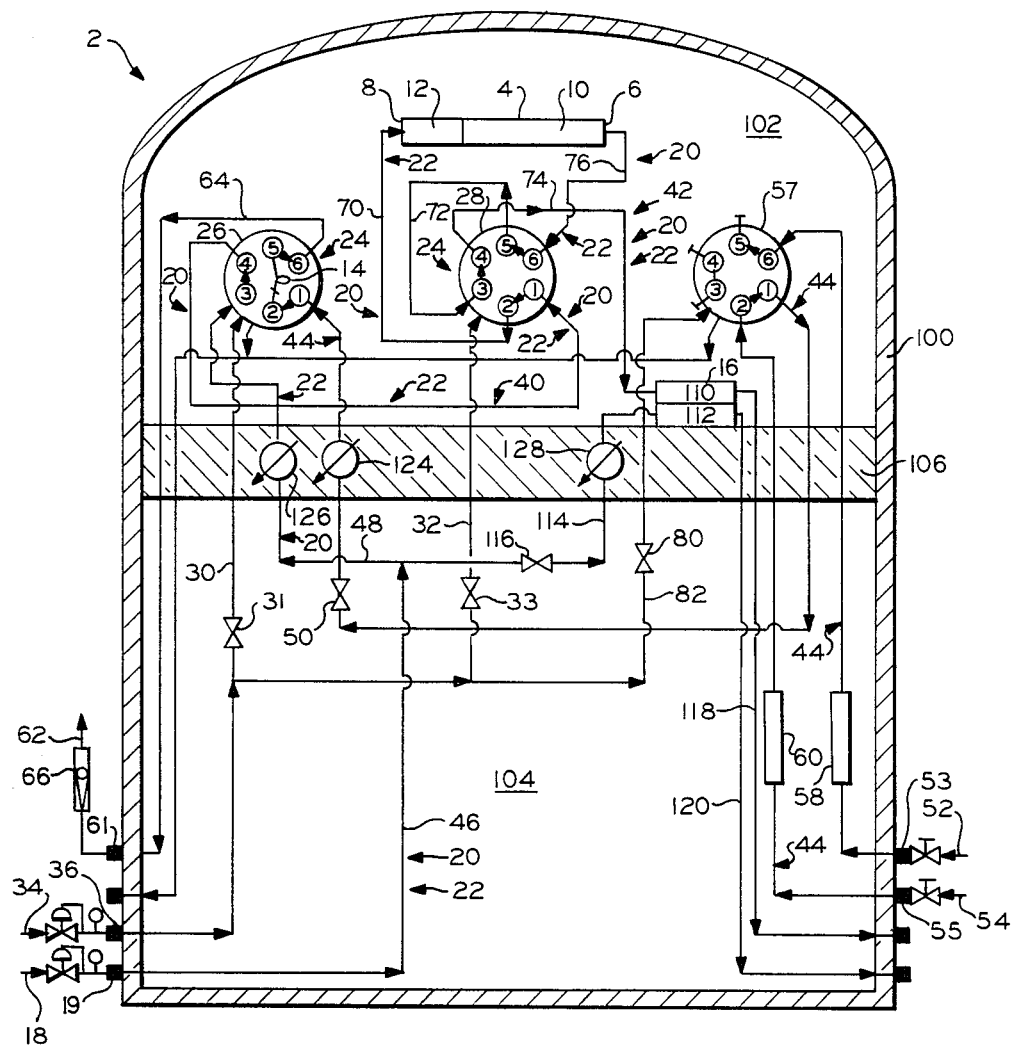
FIG. 1 schematically illustrates certain features of one embodiment of the invention.

According to certain aspects of the invention, an apparatus 2 is provided for analysis of gas samples. The apparatus 2 comprises a column 4 suitable for use in gas chromatography. Usually, column 4 will be suitable for use in high pressure gas chromatography. The column 4 has a first end 6 and a second end 8. Column 4 will frequently be formed from one or more first-end columns 10 and one or more second end columns 12. The apparatus 2 further contains a sample chamber 14 which will generally have a predetermined volume. The sample chamber 14 can conveniently be formed from a length of small diameter tubing. The apparatus is further provided with a detector 16. The detector 16 can conveniently be of the type usually employed in gas chromatography such as a low-volume thermal conductivity detector. A detector which has been used with good results contains a thermistor bead having 30 kiloohms resistance. Such a detector produces an electrical signal of varying output as different components flow through it and produces an electrical signal representative of the concentration of each component in the carrier gas stream. These electrical signals can be transmitted to a means not shown for recording in the usual manner. If desired, an operator can be applied to them in a known manner to provide a signal representative of some desired value of the sample, such as a BTU value in the case of natural gas samples. Where natural gas or a substitute is being analyzed, the sample will generally contain more than 50 percent by volume of methane gas. For use, the apparatus 2 is connected to a suitable source 18 of carrier gas, generally via a means 19 such as a fitting for connecting the carrier gas source. Generally speaking, the carrier gas source 18 will be provided from a cylinder of compressed carrier gas. When thermal type detectors are used, the carrier gas will generally comprise helium, because helium has good cooling properties as compared to the hydrocarbons and other materials such as $CO_2$ and $N_2$ to be sensed and thus provides the detector 16 with high sensitivity.

In accordance with the invention, there is provided a first means 20 for establishing a flow path from the means 19 for connecting the source of carrier gas to the sample chamber 14 and through the sample chamber 14. The means 20 further extends from the sample chamber 14 to the first end 6 of the column 4. The means 20 extends through the column 4 from the first end to the second end 8 and to the detector 16. A second means 22 establishes a flow path from the means 19 connecting the source 18 of carrier gas to the second end 8 of the column 4, through the column 4 from the second end 8 to the first end 6 and to the detector 16. For economy, the means 20 and 22 share many common parts although many of the needed parts could be maintained separate if desired. The apparatus 2 further is provided with a means 24 for selectively connecting one of the first means 20 and the second means 22 for establishing a flow path and selectively disconnecting the other. In a preferred embodiment, the means 24 is formed from a pair of double pole double throw 6 port valves 26 and 28, although other types of valves could be used readily. The ports of the valves 26 and 28 are selectively connected and disconnected by a signal from a suitable programmable controller. Preferably, a pneumatic signal is used, especially where electrically actuated valves might create an explosion hazard. In a preferred embodiment, the pneumatic signals are transmitted to the valves 26 and 28 via lines 30 and 32, respectively, which establish a flow path between a means 36 for connecting source 34 of valve gas which can be from the carrier gas cylinder if desired, and the valves 26 and 28.

In one embodiment, valves 31 and 33 are opened or closed in response to the passage of a predetermined time interval as measured by a timer means not shown. The valves 31 and 33 control the flow of valve gas to the 6-port valves 26 and 28, respectively, so as to switch the individual valves contained therein, thereby actuating the means for selectively connecting the flow paths in response to the passage of a predetermined time interval.

The invention is especially useful for making boiling point separations where elution of the higher boiling components requires considerable time, and also separations of mixtures that require several types of columns to provide different types or degrees of separation. Separation of light components generally requires considerable column length in gas chromatography and therefore the column 4 preferably has a length of at least about 10 feet. In an embodiment of the invention which has been used with good results, the upstream column 10 was formed from four 5-foot segments of 1/16 inch outside diameter, 0.032 inch inside diameter tubing formed from 316 stainless steel. These columns were packed with 100 to 120 mesh Chromosorb P (Johns-Manville) which is a diatomaceous earth from C-22 fire brick containing 20 percent by weight DC-200 which is a methyl silicone liquid available from Dow-Corning Company. The downstream column 12 was formed from a 7-foot length of the same tubing containing Porapak N available from Waters Associates which is a 100 to 120 mesh polymer of styrene and divinyl benzene which has been crosslinked. The column packing is such that when the carrier gas comprises a source of helium having a pressure of at least 100 psia, such as in the range of from 100 to 500 psia, it will undergo a pressure reduction of at least 75 percent as it passes through the column.

In another aspect of the invention, the sample chamber 14 is defined by a first tubular member 14 connected to the valve 26 and having an inlet end at port 2 and an outlet end at port 5. The column 4 suitable for use in high pressure gas chromatography has a first end 6 and a second end 8. A first means 40 defines a flow path between the sample chamber 14 and the column 4 when the valves are in the switched position from that shown in FIG. 1. The apparatus 2 is provided with a detector 16 which can be conventional. A second means 42 defines a flow path between the column 4 and the detector 16. A first valve means is positioned at the inlet end of the first tubular member 14. The valve means is switchable from a first position in which the first tubular member 14 can be connected to the means 19 for connecting the source 18 of carrier gas to a second position in which the first tubular member 14 can be connected to a source of sample gas. The source of sample gas will generally be from a stream 54 such as a pipeline or process gas stream, although it can be from an alternate gas stream 52 such as a calibration gas from a compressed gas cylinder. In the illustrated device, ports 2 and 3 of valve 26 are connected when the first valve means is in the first position and ports 2 and 1 are connected when the first valve means 14 is in the second position. The first valve means is comprised of ports 1, 2 and 3 of valve 26. In the illustrated device, a means 44 forms a flow path between the first valve means and the means 53 and 55 for connecting the gas sources 52 and 54 respectively. The means 44 includes a valve means movable from a first position in which the tubular member 14 is connected to the means 55 to a second position in which the tubular member 14 is connected to the means 53. In the illustrated device, the valve means is contained in a 6-port valve 57. Port 1 is connected to port 2 when the valve means is in the first position. Port 6 is connected to port 1 when the valve means is in the second position. The valve means comprises ports 1, 2 and 6 of 6-port valve 57. Filters 58 and 60 in the respective legs of the means 44 remove particles having a diameter of greater than about 5 to about 9 microns prior to transport of the streams 52 and 54 respectively to the 6-port valve 57. Flow rate from valve 57 to valve 26 can be controlled by manipulating a valve 50 in the means 44.

A second valve means is provided at the outlet end of the first tubular member 14. The second valve means is switchable from a first position in which the first tubular member 14 is connected to an exhaust connection 61 to a second position in which the first tubular member 14 is connected to the first means 40 defining a flow path between the sample chamber 14 and the column 4. In the illustrated device, when the second valve means at the outlet end of the tubular member 14 is in the first position, port 5 is connected to port 6. When the second valve means is in the second position, port 5 is connected to port 4. The second valve means comprises the ports 4, 5 and 6 of the valve 26. A line 64 can connect the port 6 to the connection 61 which can be in turn connected to a flow meter 66 which can be in turn connected to an exhaust 62 if desired.

Preferably, the first means 40 for defining the flow path between the tubular member 14 and the column 4 includes a third valve means which is positioned between the sample chamber 14 and the column 4. The 6-way valve 28 can serve as the third valve means. The third valve means is switchable from a first position for connecting the first means 40 for defining a flow path to the first end 6 of the column 4 to a second position in which the means 40 is connected to the second end 8 of the column 4. Preferably, when the third valve means is in the first position, port 1 is connected to port 6 of valve 28. When the third valve means is in the second position, port 1 is connected to port 2. The third valve means comprises ports 1, 2 and 6 of valve 28.

The second means 42 for defining a flow path between the column 4 and the detector 16 preferably includes a fourth valve means which is positioned between the column 4 and the detector 16. The valve 28 can serve as the fourth valve means. The fourth valve means is switchable from a first position for connecting the second end 8 of the column 4 to the detector 16 to a second position for connecting first end 6 of the column 4 to the detector 16. When the fourth valve means is in the first position, a line 70 connects the second end 8 of the column 4 to the port 2 in the valve 28. Ports 2 and 3 of the valve 28 are connected. A line 72 connects port 3 to port 5 of the valve 28. Port 5 is connected to port 4. A line 74 connects port 4 of the valve 28 with the detector 16. When the fourth valve means is in the second position, a line 76 connects the first end 6 of the column 4 with port 6 of the valve 28. Port 6 is connected to port 5. The line 72 connects port 5 to port 3. Ports 3 is connected to port 4 of the valve 28. The line 74 connects the port 4 of the valve 28 with the detector 16. The fourth valve means comprises ports 2, 3, 4, 5 and 6 of the valve 28.

In order that the apparatus 2 accomplish its intended function, it is preferably provided with a means for positioning the valves in the required position. Generally, this is accomplished by a computer which is programmed to send a signal to the valve 31 in the valve gas line 30 and/or the valve 33 in the valve gas line 32. Where automated selection is desired between the process stream 54 and the calibration stream 52, a valve 80 in a valve gas line 82 establishing a flow path between the valve 57 and the connection 36 for valve gas can also be manipulated by computer. The computer is capable to establish signals for positioning the first valve means in the first position, the second valve means in the second position, the third valve means in the first position, and the fourth valve means in the first position. The valves are maintained in these respective positions, preferably for a predetermined time interval and then the third valve means is positioned in the second position and the fourth valve means is positioned in the second position. The duration of the predetermined time interval is generally experimentally determined, depending on the composition of the column packing, pressure drop across the column, and the makeup of the gas stream for which analysis is desired. Generally speaking, where a stream containing in the range of from, say, 5 to 25 components is to be analyzed, the repositioning of the third valve means and the fourth valve means will be executed after about one quarter or one third of the peaks have been eluted.

Cycle time between runs can be further reduced by providing the apparatus with a fifth valve means which is associated with the first valve means at the inlet end of the first tubular member 14. The fifth valve means is switchable from a first position in which the first tubular member 14 can be connected to the connection 19 for carrier gas when the first valve means is in the first position to a second position in which the tubular member 14 is bypassed by the carrier gas flow and the carrier gas can be connected to the first means 40 which defined the flow path between the sample chamber 14 and the column 4 when the second valve means was in the first position. Where the 6-port valve 26 is used for the fifth valve means, the port 3 is connected to port 2 when the fifth valve means is in the first position. The first valve means will be in the first position and the ports 1 and 2 of the valve 26 will also be connected. When the fifth valve means is in the second position, the port 3 is connected to port 4 and the carrier gas will flow from the means 22 into the port 3 and out the port 4 into the means 40 leading to the column 4. The second valve means at the outlet end of the tubular member 14 will be in the second position, ports 5 and 6 of the valve 26 will be connected, and sample gas will flow past flowmeter 66. The fifth valve means comprises ports 2, 3 and 4 of the valve 26.

To make possible the refilling of the sample loop 14 with sample gas while the column 4 is in the backflush mode, the apparatus 2 is preferably provided with a means such as a computer for carrying out the following sequence of steps. The first valve means is positioned in the second position, the second valve means is positioned in the first position, the third valve means is positioned in the second position, the fourth valve means is positioned in the second position, and the fifth valve means is positioned in the second position. The apparatus 2 can be maintained in this position for as long as desired. The column will be cleansed by a backflow of carrier gas. The sample loop 14 will be cleansed by a flow therethrough of the sample gas. A new analysis of sample can then begin either upon command or in response to the passage of a predetermined period of time. For this, the first valve means is positioned in the first position, the second valve means is positioned in the first position, the third valve means is positioned in the first position, the fourth valve means is positioned in the first position, and the fifth valve means is positioned in the first position. The calibration gas sample can be analyzed if desired by actuating the switch in the valve 57 prior to carrying out the above described valving sequence.

Completing the description of the apparatus 2, the aforementioned parts and features are contained within a housing 100 which can be explosion proof or gas proof where there is an explosion hazard. The housing 100 is preferably divided into a chamber 102 which contains the column 4 and the valves 26, 28 and 57 and also the detector 16, and a chamber 104 by a partition or mandrel 106. The column 4 is preferably maintained at a controlled temperature and, for that reason, the chamber 102 is isolated and subjected to temperature control which can be by conventional means, for example. For example, the chamber 102 could be maintained at a temperature in the range of 100° to 300° F. although a temperature in the range of from about 120° to about 180° F. would be preferred for most uses. The chamber 104 is similarly under constant temperature control and will usually be at a temperature in the range of from about 50° to about 150° F., usually in the range of from about 80° to about 120° F. The detector 16 preferably has a sensing cell 110 for sample flow and a reference cell 112 for carrier gas flow such that signals from carrier gas flow through each of cells 110 and 112 will be cancelled out. Carrier gas enters cell 112 of detector 16 via line 114 which connects to the line 46. A valve 116 in the line 114 can be used to regulate carrier gas flow. A sample stream 118 is exhausted from the sample cell 110 of the detector 16. A carrier gas stream 120 is exhausted from the reference cell 112 of the detector 16. Each of the carrier gas stream to the cell 112 of the detector 16, the sample stream 44 to the sample loop 14 and the carrier gas stream 48 to the sample loop 14 or column 4, depending on the position of the fifth valve means, is preheated prior to entering the chamber 102 to provide for a stable operation of the unit. This can be accomplished by a heater 128 in the line 114, a heater 124 in the line 44 and a heater 126 in the line 48. However, in a preferred embodiment of the invention, the partition 106 is massively constructed of a material having a high heat capacity such as aluminum and the lines carrying these respective fluids are looped to provide for sufficient residence time in the partition 106 to allow for their contents to become preheated to the required temperature. Similarly, the column 4 is most preferably wrapped circumferentially around the partition 106 in a heat transfer relationship therewith so as to be maintained at a constant temperature. An insulating blanket can be used to define a chamber 102 within the housing 100 with good economy and the partition 106 heated by an electrical heater, for example.

According to certain aspects of the present invention, there is provided a process for eluting samples from a chromatographic column for analysis. A column 4 as previously described is suitable. The column can have a first end 6 and a second end 8. A carrier gas with a sample gas slug is then caused to flow from the first end 6 toward the second end 8 of the column 4 to distribute the components of the sample along the length of the column. A first fraction of the number of components is eluted from the second end of the column with the carrier gas. Generally, the first fraction of the number will be less than half of the total number of components in the sample. The first fraction of the number of components is then conveyed to a detector such as the detector 116. At that point, the carrier gas is caused to flow from the second end 8 toward the first end 6 of the column 4. The second fraction of the number of components is eluted from the first end 6 of the column and conveyed to the detector 116. The separation of the components utilizing the reverse flow of carrier gas can be enhanced when there is a high pressure drop between the first end and the second end of the column. Generally speaking, the pressure drop through the column will range from 100 to 500 pounds per square inch, the pressure at the low pressure end of the column being at atmospheric. However, the invention can be practiced where the pressure drop through the column is such that the low pressure into the column is at a pressure of less than 25 percent of the pressure at the high pressure end. Preferably, the pressure drop on the carrier gas between the ends of the columns will be such that the low pressure end of the column is at a pressure of less than about 15 percent of the pressure of the high pressure end of the column. If desired, a vacuum can be applied to the downstream end of the detector to further increase the pressure drop through the column. The pressure at the low pressure end of the column will generally be maintained in the range of 0.2 to about 20 pounds per square inch, absolute. Usually, the desired separation can be obtained by using a boiling point column in accordance with the invention. The components in the first fraction of the number of components which are recovered from the second end of the column will be eluted in order of increasing boiling point. The components in the second fraction of the number of components which are eluted from the first end of the column will preferably be eluted in decreasing boiling point order, although once the component peaks are identified, their passage to a detector need not be in reverse boiling point order. The point at which reverse flow procedure should be initiated is best determined experimentally. Once the determination has been made on the point at which to initiate backflow of carrier gas and obtain the desired resolution in the desired time frame, flow reverse will preferably be actuated by a timer.

In certain other aspects of the invention, there is provided a process comprising flowing a gaseous sample comprised of light components and heavy components into a sample chamber. The distinction between the light components and the heavy components is made in hindsight, depending on whether the components are eluted from the column in a forward flow or in reverse flow. By definition herein, the light components are those which are eluted from the column in the forward flow mode and the heavy components are those which are eluted from the column in the reverse flow mode. A first flow of carrier gas is flowed through the sample chamber and into the first end of a chromatographic column which has a first end and a second end to carry the sample to the first end. The light components are then eluted from the second end of the chromatographic column with the flow of carrier gas. The flow of carrier gas through the column is stopped. A second flow of carrier gas through the column is then initiated which carries from the second end of the column to the first end of the column. The heavy components of the sample are then eluted from the first end of the chromatographic column and the second flow of carrier gas is terminated, after a time interval to flush the column with carrier gas if desired or, in any event, prior to reuse of the column.

Preferably, the time of flow of the first flow of carrier gas is measured and the first flow of carrier gas through the column is terminated after the passage of a predetermined time interval. The predetermined time interval, as previously discussed, is best determined experimentally. To provide a simple system capable of making repetitive measurements, it is also desirable to measure the time of flow of the second flow of carrier gas and terminate the second flow of carrier gas after a predetermined time interval. The second predetermined time interval is after a period of time sufficient to clear the column 4 of sample components. In a preferred embodiment, the chromatographic system of the invention is employed in the calculation of the BTU (British Thermal Unit) content or heating value of natural gas or synthetic natural gas. In such an event, the sample to be analyzed will generally contain more than 50 percent by volume of methane gas. In the practice of this embodiment, the eluted light components and the eluted heavy components are conveyed to a detector and an electrical signal generated from the detector which is representative of the concentrations of each component in the carrier gas stream. These signals can then be transformed by a suitable device into a signal which is representative of the heating value of the sample using known correlations. In a system for the analysis of the components of natural gas which has been used with good results, the light components of the sample are eluted from the second end of the column in order of increasing boiling point and the heavy components are eluted from the first end of the column in order of decreasing boiling point. The high efficiency of this system is believed due at least in part to the maintenance of a pressure drop between the ends of the column, such that the pressure at the low pressure end of the column is less than about 25 percent of the pressure at the high pressure end of the column, preferably less than about 15 percent of the pressure at the high pressure end of the column. The invention is illustrated by the following example.

EXAMPLE

Equipment used:
Chromatograph: Model 12 gas chromatograph system, Applied Automation, Inc., Bartlesville, OK.
Column 4: 4×5 ft. sections of 316 stainless steel tubing 1/16 inch O.D., 0.032 inch I.D. Packed with Dow Corning's DC-200 fluid on Chromosorb P (Johns-Manville) in series with a 7 ft. section of 1/16 inch O.D., 0.032 inch I.D. 316 stainless steel tubing packed with Waters Assoc. Porapak N.
Pressure Drop Thru Total Column: 140–145 psig. both ways.
Carrier Flow Rate Thru Total Column Both Ways: 8 cc/minute.
Sample Loop 14 Volume: 0.170 cc.
Carrier: He.
Sample: Natural gas (synthesized).
Sample Valves 26,28 and 57: Model XI, Applied Automation, Inc.
Recorder: Leeds & Northrup, Speedomax H.
Chart Speed: 1 inch/minute (left to right) (when viewed from base).
Chart Nomenclature:
Large negative glitches are points of valve switching.
Small positive and negative glitches are integrator start/stop points.

Figure 2:
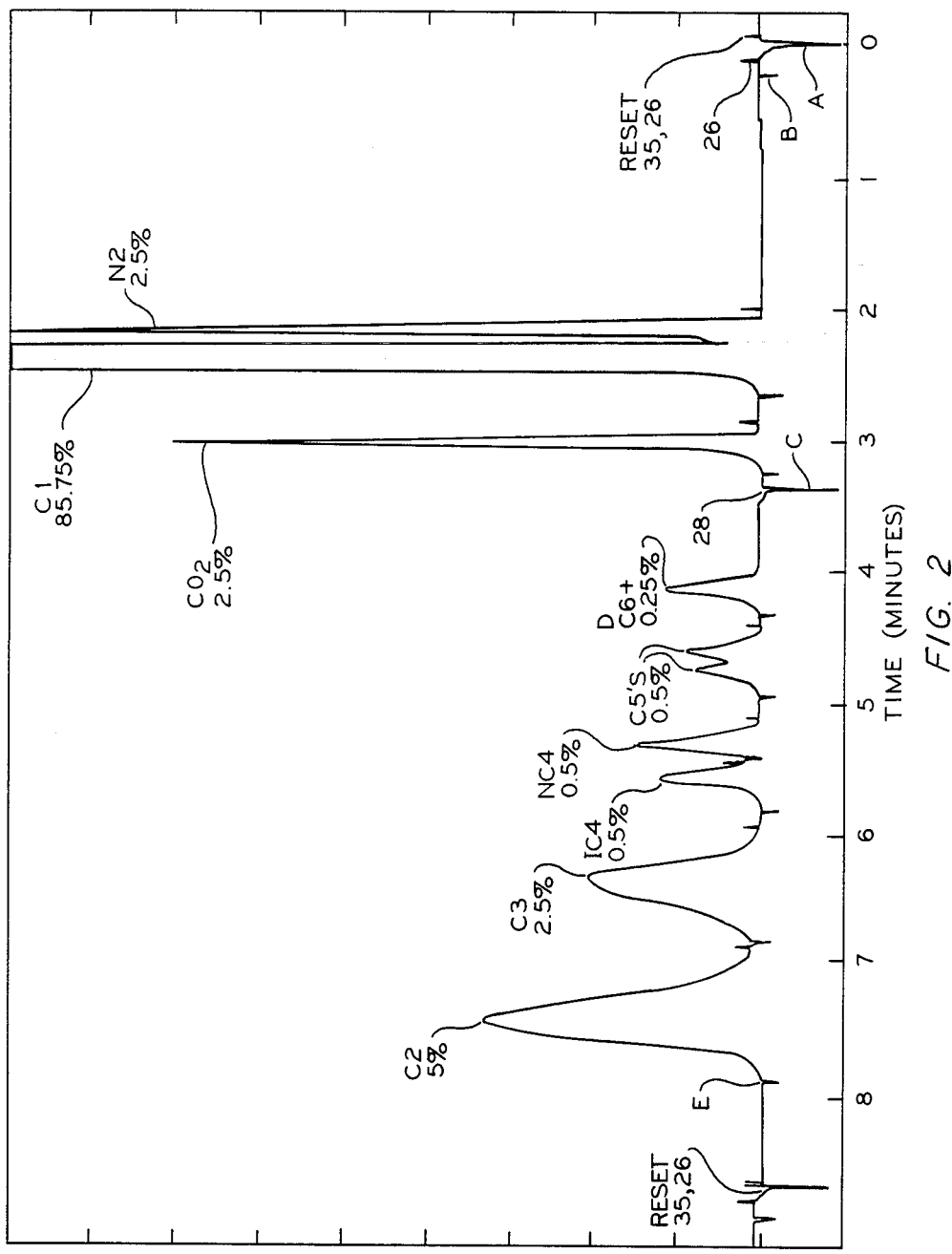
FIG. 2 illustrates a separation carried out by the invention.

Referring now to FIGS. 1 and 2 and noting that valves 26,28 and 57 are shown in their OFF positions respectively, At TIME(T)=0 seconds, POINT A, fresh sample is flowing in sample loop 14 and valve 28 is switched ON. At T=8 seconds, valve 26 is switched ON. Carrier gas now sweeps the sample from loop 14 to valve 28 to said first end 6 of column 4, out said second end 8 of column 4 to valve 28 to detector 16. At POINT B, T=16 seconds, valve 26 is switched OFF and is purged with fresh sample. At T=3 minutes 20 seconds approximately (actual time is determined experimentally), POINT C, after $CO_2$ has eluted detector 16, valve 28 is switched OFF to result in reversing the flow of carrier gas thru column 4 to the detector. This further results in the elution of the heavier components of the sample from column 4 to the detector 16, the heaviest component, C6+, eluting first as shown at POINT D. It should be noted that from POINT B sample components are eluted in the order of increasing density. From POINT C to POINT E, sample components are eluted in the order of decreasing density. If forward passage of the sample were continued thru the column from POINT C to POINT E, then the recorded positions of C6 through C2 would be reversed and the elution time would be approximately doubled from that shown in FIG. 2. After the last peak elutes from the detector, the cycle starts over. Calibration of the system can be effected via switching of valve 57 to its ON position which will result in the utilization of a sample gas of known composition (from source 52) in one or more cycles.

What is claimed is:
1. A process comprising:
 (a) introducing a gaseous sample comprised of a number of components into a first end of a chromatographic separation column having a first end and a second end;
 (b) flowing a carrier gas toward the second end of the column to distribute the components of the sample along the length of the column;

(c) eluting a first fraction of the number of components from the second end of the column with the carrier gas;

(d) conveying the first fraction of the number of components to a detector;

(e) flowing the carrier gas from the second end toward the first end of the column to establish a nonlinear flow velocity profile along the column such that gas velocity is faster at the first end of the column that at the second end of the column;

(f) eluting a second fraction of the number of components from the first end of the column; and (g) conveying the second fraction of the number of components to the detector.

2. A process comprising:
(a) flowing a gaseous sample comprised of light components and heavy components into a sample chamber;

(b) flowing a first flow of carrier gas through the sample chamber and into the first end of a chromatographic column having a first end and a second end to carry the sample to the first end of the chromatographic column;

(c) eluting the light components of the sample from the second end of the chromatographic column with the first flow of carrier gas, wherein the light components of the sample are eluted in the order of increasing boiling points;

(d) stopping the first flow of carrier gas;

(e) flowing a second flow of carrier gas from the second end of the chromatographic column to the first end of the chromatographic column;

(f) eluting the heavy components of the sample from the first end of the chromatographic column, wherein the heavy components of the sample are eluted in the order of decreasing boiling points; and (g) stopping the second flow of carrier gas.

3. A process as in claim 2 further comprising
(a) measuring the time of flow of the first flow of carrier gas; and
(b) stopping the first flow of carrier gas after the passage of a predetermined time interval.

4. A process as in claim 3 further comprising
(a) measuring the time of flow of the second flow of carrier gas; and
(b) stopping the second flow of carrier gas after the passage of a second predetermined time interval.

5. A process as in claim 3 wherein the sample contains more than 50 percent by volume of methane gas.

6. A process as in claim 3 further comprising conveying the eluted light components and eluted heavy components to a detector and generating an electrical signal representative of the concentration of each component in the carrier gas stream.

7. A process as in claim 6 further comprising transforming the electrical signals into a signal representative of the heating value of the sample.

8. A process comprising:
(a) introducing a gaseous sample comprised of a number of components into a first end of a chromatographic separation column having a first end and a second end;

(b) flowing a carrier gas toward the second end of the column to distribute the components of the sample along the length of the column, wherein the carrier gas flow is caused by a pressure drop between the first end and the second end of the column such that the second end of the column is at a pressure of less than 25 percent of the pressure at the first end of the column;

(c) eluting a first fraction of the number of components from the second end of the column with the carrier gas;

(d) conveying the first fraction of the number of components to a detector;

(e) flowing the carrier gas from the second end toward the first end of the column, wherein the carrier gas flow is caused by a pressure drop between the second end and the first end of the column such that the first end of the column is at a pressure of less than 25 percent of the pressure at the second end of the column;

(f) eluting the second fraction of the number of components from the first end of the column; and (g) conveying the second fraction of the number of components to the detector.

9. A process as in claim 8 wherein the pressure drop on the carrier gas between the high pressure end and the low pressure end of the column is such that the low pressure end of the column is at a pressure of less than about 15 percent of the pressure at the high pressure end of the column.

10. A process as in claim 8 wherein the pressure at the high pressure end of the column is in the range of 50–500 pounds per square inch, absolute, and the pressure at the low pressure end of the column is in the range of 0.2 to about 20 pounds per square inch, absolute.

11. A process as in claim 8 wherein the column is a boiling point column, said process further comprising eluting the components in the first fraction of the number of components from the second end of the column in increasing boiling point order and eluting the components from the first end of the column in decreasing boiling point order.

12. A process as in claim 11 wherein the column has a length of at least about 10 feet.

13. A process comprising:
(a) flowing a gaseous sample comprised of light components and heavy components into a sample chamber, wherein the gaseous sample contains more than 50 percent by volume of methane gas;

(b) flowing a first flow of carrier gas through the sample chamber and into the first end of a chromatograph column having a first end and a second end to carry the sample to the first end of the chromatograph column;

(c) maintaining a pressure drop between the ends of the column such that the pressure at the low pressure end of the column is less than 25 percent of the pressure at the high pressure end of the column;

(d) eluting the light components of the sample in the order of increasing boiling point from the second end of the chromatograph column with the first flow of carrier gas;

(e) conveying the eluted light components to a detector and generating an electrical signal representative of the concentration of each light component in the carrier gas stream;

(f) stopping the first flow of carrier gas after the passage of a first predetermined time interval;

(g) flowing a second flow of carrier gas from the second end of the chromatographic column to the first end of the chromatographic column;

(h) eluting the heavy components of the sample from the first end of the chromatographic column in the order of decreasing boiling point;
(i) conveying the eluted heavy components to the detector and generating an electrical signal representative of the concentration of each heavy component in the carrier gas stream;
(j) stopping the second flow of carrier gas after the passage of a second predetermined time interval; and
(k) transforming the electrical signals into a signal representative of the heating valve of the gaseous sample.

14. A process as in claim 13 wherein the pressure at the low pressure end of the column is less than 15 percent of the pressure at the high end of the column.

15. Apparatus comprising:
(a) a column suitable for use in high pressure gas chromatography, said column having a first end and a second end, and having a length of at least about 10 feet;
(b) a sample chamber having a predetermined volume;
(c) a detector;
(d) means for connecting a source of carrier gas;
(e) first means for establishing a flow path from the means for connecting the source of carrier gas to the sample chamber, through the sample chamber and to the first end of the column, through the column from first end to second end and to the detector;
(f) second means for establishing a flow path from the means for connecting the source of carrier gas to the second end of the column, through the column from second end to first end, and to the detector; and
(g) means for selectively connecting one of the first means for establishing a flow path and the second means for establishing a flow path and selectively disconnecting the other;
(h) timer means associated with the means for selectively connecting one of means to establishing flow paths so as to actuate the means for selectively connecting in response to the passage of a predetermined time interval.

16. Apparatus comprising:
(a) a column suitable for use in high pressure gas chrmatography comprising a first section packed with a supported methyl silicon liquid and a second section packed with a crosslinked polymer of styrene and divinyl benzene, said column having a first end and a second end;
(b) a sample chamber having a predetermined volume;
(c) a detector;
(d) means for connecting a source of carrier gas;
(e) first means for establishing a flow path from the means for connecting the source of carrier gas to the sample chamber, through the sample chamber and to the first end of the column, through the column from first end to second end and to the detector;
(f) second means for establishing a flow path from the means for connecting the source of carrier gas to the second end of the column, through the column from second end to first end, and to the detector; and (g) means for selectively connecting one of the first means for establishing a flow path and the second means for establishing a flow path and selectively disconnecting the other.

17. An apparatus as in claim 16 further comprising a timer means associated with the means for selectively connecting one of means to establishing flow paths so as to actuate the means for selectively connecting in response to the passage of a predetermined time interval.

18. An apparatus as in claim 16 wherein the column packing is 100 to 120 mesh size.

19. Apparatus comprising:
(a) a sample chamber defined by a tubular member having an inlet end and an outlet end;
(b) a column suitable for use in high pressure gas chromatography, said column having a first end and a second end;
(c) first means for defining a flow path between the sample chamber and the column;
(d) a detector;
(e) second means for defining a flow path between the column and the detector;
(f) first valve means at the inlet end of the tubular member, said first valve means being switchable from a first position in which the tubular member can be connected to a source of carrier gas to a second position in which the tubular member can be connected to a source of sample:
(g) second valve means at the outlet end of the tubular member, said second valve means being switchable from a first position in which the tubular member is connected to an exhaust to a second position in which the tubular member is connected to the first means for defining a flow path between the sample chamber and the column;
(h) third valve means positioned in the first means for defining a flow path between the sample chamber and the column, said third valve means being switchable from a first position for connecting the first means for defining a flow path to the first end of the column to a second position for connecting the first means for defining a flow path to the second end of the column; and
(i) fourth valve means positioned in the second means for defining a flow path between the column and the detector, said fourth valve means being switchable from a first position for connecting the second end of the column to the detector to a second position for immediately connecting the first end of the column to the detector.

20. Apparatus as in claim 19 further comprising a means for the following:
(a) positioning the first valve means in the first position, the second valve means in the second position, the third valve means in the first position, and the fourth valve means in the first position; and
(b) continuing step (a) for a predetermined time interval and then positioning the third valve means in the second position and the fourth valve means in the second position.

21. Apparatus as in claim 20 further comprising a fifth valve means associated with the first valve means at the inlet end of the first tubular member, said fifth valve means being switchable from a first position in which the first tubular member can be connected to the source of carrier gas when the first valve means is in the first position to a second position in which the carrier gas can be connected to the first means for defining a flow path between the sample chamber and the column when the second valve means is in the first position.

22. Apparatus as in claim 21 further comprising a means for the following:
(a) positioning the first valve means in the second position, the second valve means in the first position, the third valve means in the second position, the fourth valve means in the second position, and the fifth valve means in the second position; and then upon command or in response to the passage of a predetermined period of time;
(b) positioning the first valve means in the first position, the second valve means in the first position, the third valve means in the first position, the fourth valve means in the first position, and the fifth valve means in the first position.

* * * * *